United States Patent

Sunde et al.

Patent Number: 5,717,131
Date of Patent: Feb. 10, 1998

[54] APPARATUS FOR TESTING A SHEAR THICKENING PLUGGING FLUID

[75] Inventors: Egil Sunde, Sandnes; Hans Konrad Johnsen, Stjordal; Tommy Engan, Skarval, all of Norway

[73] Assignee: Den norske stats oljeselskap a.s., Stavanger, Norway

[21] Appl. No.: 628,622

[22] PCT Filed: Oct. 11, 1994

[86] PCT No.: PCT/NO94/00163

§ 371 Date: Apr. 10, 1996

§ 102(e) Date: Apr. 10, 1996

[87] PCT Pub. No.: WO95/10764

PCT Pub. Date: Apr. 20, 1995

[30] Foreign Application Priority Data

Oct. 12, 1993 [NO] Norway ......... 933677

[51] Int. Cl.⁶ ......... G01N 11/00; E21B 33/138; C09K 7/02; C08L 3/34
[52] U.S. Cl. ......... 73/64.41; 73/53.01; 73/61.73; 73/152.39; 166/285; 166/281; 166/270
[58] Field of Search ......... 73/53.01, 61.41, 73/61.73, 53.04, 152.39, 152.37, 152.55; 166/281, 285, 270

[56] References Cited

U.S. PATENT DOCUMENTS

| | | | |
|---|---|---|---|
| 4,183,406 | 1/1980 | Lundberg et al. | 166/295 |
| 4,344,321 | 8/1982 | Haapamaki | 73/61.4 |
| 4,391,925 | 7/1983 | Mintz et al. | 523/130 |
| 4,445,576 | 5/1984 | Drake et al. | 166/291 |
| 4,663,366 | 5/1987 | Drake et al. | 523/130 |
| 4,663,966 | 5/1987 | Fisher et al. | 73/61 R |
| 4,754,639 | 7/1988 | Rich et al. | 73/53 |
| 4,933,886 | 6/1990 | George | 364/556 |
| 5,104,912 | 4/1992 | Hoskin | 523/130 |
| 5,257,528 | 11/1993 | Degouy et al. | 73/53.01 |
| 5,271,521 | 12/1993 | Noss et al. | 221/1 |
| 5,309,761 | 5/1994 | Ravi et al. | 73/151 |
| 5,319,958 | 6/1994 | Date et al. | 73/53.01 |
| 5,347,851 | 9/1994 | Grudzien, Jr. et al. | 73/53.01 |
| 5,621,163 | 4/1997 | Johnson | 73/38 |

FOREIGN PATENT DOCUMENTS

| | | |
|---|---|---|
| 0 435 713 A1 | 11/1990 | European Pat. Off. |
| WO 81/00874 | 4/1981 | WIPO |
| WO 94/28085 | 12/1994 | WIPO |

Primary Examiner—Hezron E. Williams
Assistant Examiner—J. David Wiggins
Attorney, Agent, or Firm—Kirkpatrick & Lockhart LLP

[57] ABSTRACT

An apparatus for testing a shear thickening plugging fluid that is an emulsion of two components which react with each other to provide a thickening of the fluid when subjected to high stress, such apparatus comprising a cylinder (1) having an inlet (2) with an inlet valve (3) for the plugging fluid and an outlet (4) with an outlet valve (5) for the plugging fluid, a moveable piston (6) sealing against the chamber walls, so that the piston by being moved rearward in the cylinder can suck plugging fluid into the cylinder through the inlet (2), and in a retrograde movement can press the plugging fluid out through the outlet (4), a shear valve (7) connected with the outlet (4), which shear valve (7) is adjustable for adjusting a desired shear stress to be subjected upon the plugging fluid, a means (8, 9) for measuring the pressure drop over the shear valve (7), a receiver means (10) for collecting plugging fluid that has been pressed through the shear valve, and one or more means for measuring properties of the shear thickening plugging fluid.

20 Claims, 2 Drawing Sheets

APPARATUS FOR TESTING A SHEAR THICKENING PLUGGING FLUID

BACKGROUND OF THE INVENTION

1. Field of the Invention

The present invention relates to an apparatus for the testing of different properties of a shear thickening plugging fluid useful for plugging of a zone of a subterranean formation around a well bore, or for blocking a well in case of unintended water intrusion. The properties of a plugging fluid that it may be of particular interest to evaluate are in particular related to setting time, shear strength and homogeneity at different pressure and temperature conditions and chemical conditions.

2. Description of the Invention Background

For plugging of zones of subterranean formations, a use may be made i.a. of so-called "rheotropic" fluids, which fluids thicken when subjected to high shear. A suitable rheotropic fluid for such use is a fluid having physical properties enabling it to be easily pumped through the mud system (Condition 1) to the drill bit, and to set (Condition 2) when forced through the nozzles of the drill bit, where the pressure drop will be in the range of about 50 to 120 bars. Also, the time period from the passing through the nozzles till setting takes place must be sufficiently long to enable the fluid to flow into the formation zones to be plugged.

For the preparation of a plugging fluid having such desired setting pattern, it is known to use an emulsion technique for preparing an emulsion in which two reactive components—which will provide a thickening or setting of the fluid when brought in contact with one another—are placed each in one separate phase of the emulsion, in such a way that they are not brought into contact with one another. As long as the emulsion is not broken, the two reactive components will in this manner stay separated from one another, whereby the emulsion maintains its original low viscosity. On the other hand, when the emulsion is subjected to high shear, causing it to be broken, the two reactive components will come into contact with one another and the setting of the fluid takes place.

Said emulsion technique can be utilized in several ways. Thus, U.S. Pat. No. 4,663,366 discloses a rheotropic water-in-oil emulsion wherein (a) the oil phase contains dispersed therein a hydratable water-swelling hydrophilic clay such as bentonite, and also contains dissolved therein a surfactant consisting of a polyamine derivative, and (b) the water phase contains dissolved therein a polyacrylamide and a polycarboxylic acid. To keep the bentonite separated from the water until a setting of the fluid is desired, each droplet of the dispersed aqueous phase is coated with a membrane or a film of a polymer material which is formed when the aqueous phase is dispersed or emulsified into the oil phase of the emulsion. The film or membrane is formed as a result of the interfacial interaction between the polyamine derivative in the oil phase and the polyacryl amide and polycarboxylic acid in the dispersed aqueous phase. When the emulsion is subjected to high shear stress at the desired point of time, the protective film around the dispersed droplets in the emulsion is broken and the bentonite comes into contact with the water, which leads to a swelling of the bentonite and consequently a thickening of the fluid.

A plugging fluid in which the emulsion technique has been utilized in a different manner is disclosed in Norwegian Patent Application No. 931954. This plugging fluid is constituted of an emulsion comprising (a) a continuous phase containing a hydrophobic liquid (oil), an emulsifier and a cross-linking agent for a polysaccharide, and (b) a discontinuous phase containing water and a polysaccharide. In this case, the mechanism of the setting of the plugging fluid is a cross-linking of the polysaccharide with the cross-linking agent. Thus, for achieving the desired effect of the plugging emulsion it is critical even in this case that the two reactive components of the emulsion are kept separated from one another until a setting of the plugging emulsion is desired. This separation is achieved by maintaining the cross-linking agent incapsulated in the hydrophobic liquid (e.g. an oil), while the polysaccharide is incorporated in the discontinuous phase of the emulsion, which phase is an aqueous phase. Consequently, as long as the emulsion is at rest or is subjected to moderate shear stress only, no substantial cross-linking reaction will occur. However, when the emulsion is subjected to a high shear stress, as when squeezed through a drill bit in a borehole, the polysaccharide and the cross-linking agent will come into contact with one another, whereby a cross-linking of the polysaccharide takes place and the plugging emulsion sets.

The mud system employed in well and formation treatment operations consists of a number of units, each of which exerts shear stress to a greater or lesser extent on the fluids pumped through the system. The shear stress is closely related to the pressure drop in each individual unit. The highest pressure drop, and thus the highest shear stress, occurs e.g. during the passage through the nozzles of a drill bit or through a port in a completion string down in the well. The use of plugging fluids for the intended purpose is based on the condition that only flow restrictions down in the well should be capable of producing a sufficiently high shear stress for the two reactive components, each of which is contained in a separate phase of the emulsion, to be brought into contact with one another, with a resulting thickening/setting of the fluid.

For the plugging fluid to fulfill its purpose down in the formation, it is important (1) that it has the lowest possible viscosity in Condition 1, before it is subjected to high shear stress, (2) that it thickens to a high thickness in Condition 2 after having been subjected to a high shear stress, (3) that it maintains its acquired thickness for a desired period of time, and (4) that it undergoes to the least possible extent a thickening in Condition 1 as a result of the emulsion gradually deteriorating during storage or before it has been passed through the nozzles in the drill bit or other flow restrictions down in the borehole.

In order to secure that a plugging fluid fulfills its function to the largest possible extent down in the formation, it may be desirable to test the plugging fluid before it is injected into the borehole. In particular, it is important to be able to recreate the shear stress to which the plugging fluid will be exposed down in the borehole, because the setting time as well as the stiffness of the formed gel will depend on the shear stress to which the emulsion has been subjected.

When a liquid is flowing through a nozzle there will be a close correlation between the pressure drop through the nozzle and the shear stress to which the liquid is subjected in the nozzle. It would therefore be possible, by using scaled down nozzle sizes, to achieve a good simulation of the conditions down in the well bore and thus predict with a high probability how the plugging fluid will behave in practice. A testing apparatus capable of giving a realistic picture of the shear stress to which a fluid would be exposed when squeezed through e.g. the nozzles in a drill bit down in a well bore should be equipped with a means for creating a pressure drop in the fluid of up to 120 bars, especially a pressure drop of 30 to 100 bars, and it would be practical to carry out the testing of the plugging fluid on the basis of fluid volumes of the order of 0.5 to 2.0 liters.

Also, an apparatus for testing rheotropic plugging fluids should be designed so as to prevent the fluid from being subjected to undesired shear stress and to prevent the apparatus from being exposed to excessive wear caused by solid particles contained in the fluid.

SUMMARY OF THE INVENTION

According to the present invention an apparatus is provided for use in testing a shear thickening plugging fluid, which apparatus fulfills said desires. The apparatus is characterized by the features set forth in claim 1.

BRIEF DESCRIPTION OF THE DRAWINGS

The apparatus and its operation is described below with reference to the appended drawings, which schematically illustrate preferred embodiments of the apparatus.

DETAILED DESCRIPTION OF THE PREFERRED EMBODIMENTS

Figure 1:
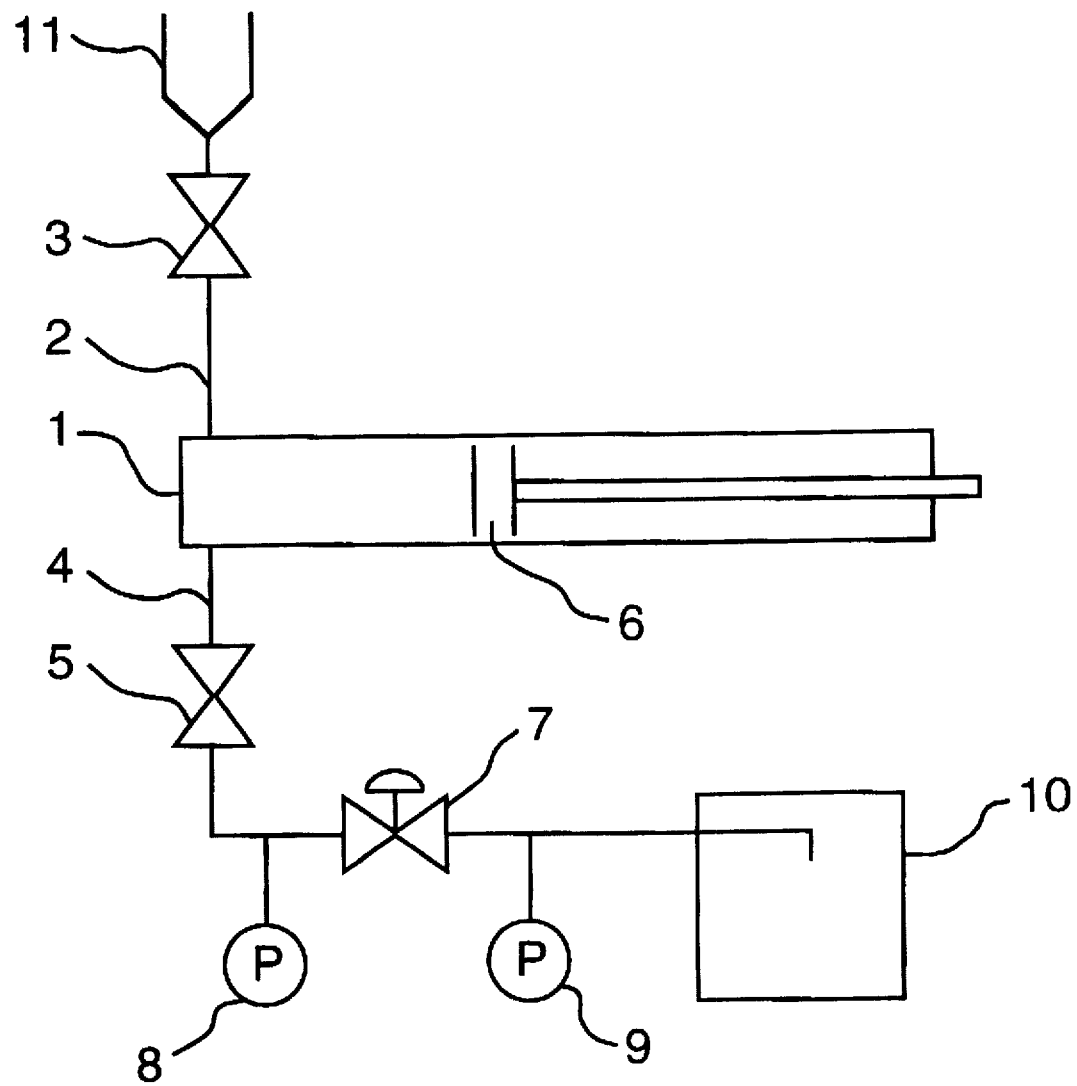
FIG. 1 is a schematic illustration of the apparatus of the present invention.

FIG. 1 shows a cylinder 1 which is connected, via an inlet 2 at one end thereof and an inlet valve 3, with a hopper 11 for plugging fluid to be tested, which plugging fluid is fed into said hopper from a mixing apparatus (not shown). At the same end the cylinder 1 has a plugging fluid outlet 4 which is connected with an adjustable shear valve 7 via an outlet valve 5. In front of and behind the shear valve, means 8, 9 are arranged for measuring the pressure at the upstream and downstream sides of the shear valve, respectively. A container 10 is arranged for collecting plugging fluid from the shear valve 7. A piston 6 in cylinder 1 is sealing against the cylinder wall and is moveable therein. Thus, by moving the piston in the cylinder, plugging fluid is sucked into the cylinder through inlet 2 and in a retrograde movement of the piston the plugging fluid is pressed out through the outlet 4. The piston is preferably driven by a hydraulic aggregate (not shown). The shear valve utilized in the apparatus can suitably be a needle valve and valves 3 to 5 can suitably be ball valves.

The apparatus is operated in the following manner. The cylinder 1 is filled with plugging fluid from the hopper 11 by the inlet valve 3 being opened and the piston 6 being pulled into the cylinder from its end position at inlet 2 and outlet 4, while the outlet valve 5 is maintained in a closed position. When the piston has reached the opposite end position and the available cylinder volume has been filled with plugging fluid, the inlet valve 3 is shut and the outlet valve 5 is opened. The piston is then returned to the first-mentioned end position, whereby the plugging fluid is squeezed out of the cylinder through the outlet 4 and further through the outlet valve 5 and the shear valve 7 and into a receiver container 10. In the adjustable shear valve 7 the plugging fluid is subjected to a predetermined shear stress resulting in a breaking of the emulsion and initiation of the setting process. The shear stress is related to the pressure difference over the shear valve, i.e. to the difference between the pressures measured by pressure-gauges 8, 9 in front of and behind the shear valve, respectively. By using a plugging fluid according to Norwegian Patent Application No. 931954, the setting will occur as a result of the cross-linking agent coming into contact with the polysaccharide and causing a cross-linking thereof. However, the setting does not occur spontaneously, however, and the plugging fluid can thus easily flow into the receiver container wherein the setting then takes place.

In the receiver container 10, properties of the fluid such as the setting time and stiffness (shear strength) of the formed gel are measured in manner known per se.

In the simplest case, the receiver container 10 is an open container which is filled with the sheared plugging fluid, and the shear strength of the gel is measured by means of standard geotechnical methods.

It may also be of interest, however, to perform the shearing of the plugging fluid against a pressure and to let the fluid set under pressure. In such a case, a pressure container is used as the receiver means. In order to allow collection of the plugging fluid from the shear valve, the pressure container must be equipped for withdrawal of its initial content under a controlled pressure. In this case, the measuring of the shear stress can be carried out either at atmospheric pressure, in which case the container is depressurized at the desired point of time and the measurements are carried out at atmospheric pressure as mentioned above, or under an overpressure, in which case the pressure container will be equipped with a high pressure consistometer equipped for shear strength measurement.

In order to achieve measuring results giving an even better picture of the behaviour of the plugging fluid when being positioned in the formation zone to be plugged, it may be desirable to collect the sheared plugging fluid in a receiver container containing one or more solid, permeable materials with a selected porosity and permeability. With a knowledge of the conditions in the formation zone, one can recreate said conditions approximately and determine with an approximate accuracy the plugging capacity of any particular plugging fluid in said zone. With a receiver container containing such solid permeable material, the shear strength measurements can be carried out with means for measuring the maximum differential pressure which the contents of porous material and set plugging fluid in the receiver container are capable of withstanding before the set plugging fluid collapses.

Figure 2:
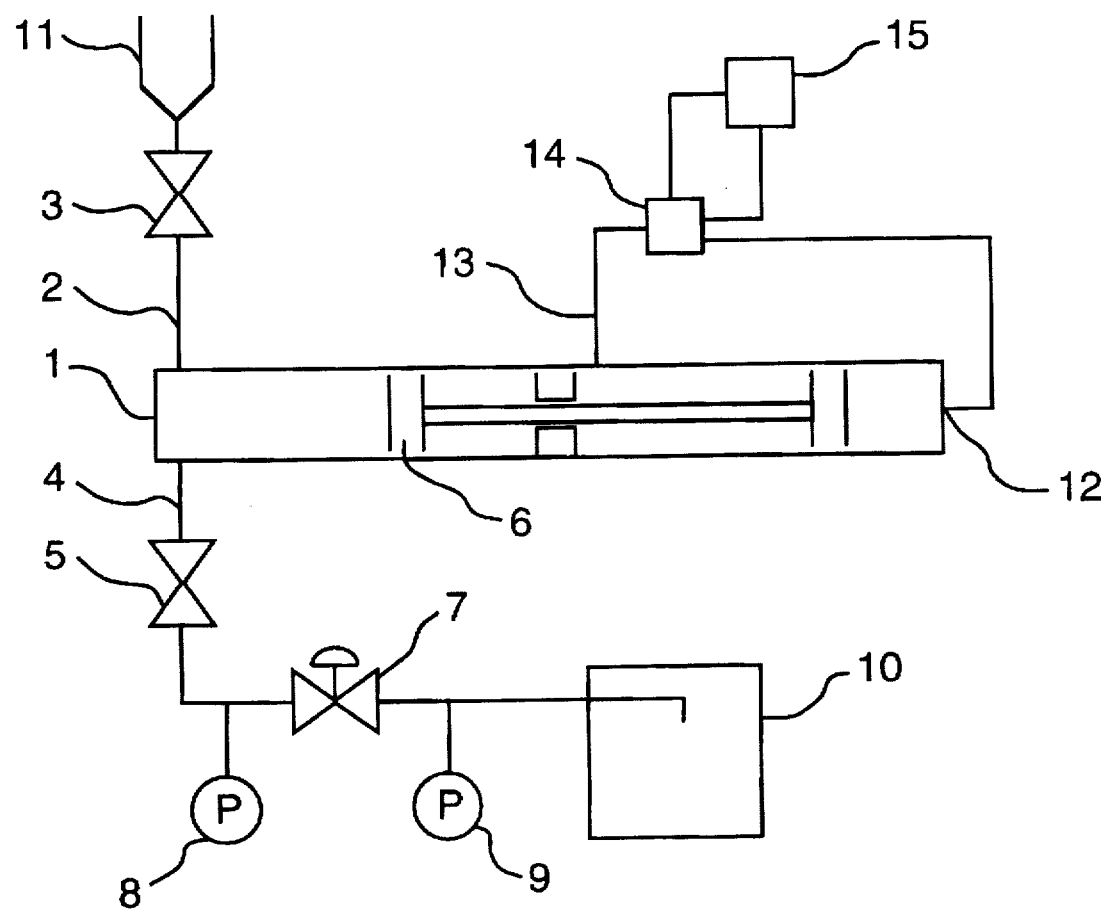
FIG. 2 is a schematic illustration of a hydraulic embodiment of the apparatus of the present invention.

A hydraulic embodiment of the apparatus of the invention is shown schematically in FIG. 2, where those reference numerals which also occur in FIG. 1 have the same meaning as as in FIG. 1. In this case, cylinder 1 is a double-acting hydraulic cylinder which contains a drive piston (16) which is connected with, a working piston 6 via a piston rod (17). The drive piston is driven by a hydraulic aggregate comprising a hydraulic pump 15, a control valve 14 and inlet 12 and outlet 13 for hydraulic oil. The receiver means 10 and the means used for performing the measurements may be similar to those described with reference to FIG. 1.

The apparatus according to the invention may advantageously be constructed as a mobile unit. The piston 6 would then suitably be hydraulically driven and the hydraulic pump 15 used to drive the piston 6 would be arranged in a separate casing and be connected to the apparatus by means of a hydraulic quick release coupling.

EXAMPLE

The object was to predetermine the setting characteristics obtained with a given shear thickening plugging fluid when being squeezed at a pressure drop of 60 bars through the nozzles of a drill bit down in a well bore.

For this purpose a test apparatus as shown schematically in the appended FIG. 2 was used. The cylinder of the apparatus had an internal diameter of 65 mm and a neat volume of about 1.0 liter. The effective stroke length of the piston was 300 mm. The piston was driven by a hydraulic unit of trademark Hidroirma, Type UP10; P=105 bars; Q=3.0 l/min. The shear valve was a 10 mm needle valve of trademark Nupro, Type SS-4R3A5. The piping for transport of the plugging fluid from the hopper via the cylinder and the shear valve to the receiver container was of stainless steel SS 316 L and had an internal diameter of 10 mm. As inlet and outlet valves upstream and downstream of the cylinder, respectively, 10 mm ball valves of trademark Whitey, Type 44-S 10 MN were used. The receiver container was an open container and the shear strength measurements were effected with a shear strength measuring instrument of the trademark Sinco Torvane, Model 51602.

For use as a plugging fluid 1.375 liters of water-in-oil emulsion were prepared in the following manner. 0.75 of water and 6.0 g of xanthane were mixed with agitation in a 2 l beaker (beaker 1). After 1 hour at rest 1500 g of barite were added to the mixture. In a second 2 l beaker (beaker 2) 0.25 l of Exxsol D60, 1.0 ml of Safemul PE (an emulsifier on triglyceride basis) and 8.0 g of $Ca(OH)_2$ were mixed with agitation. The mixture in beaker 1 was then added to the mixture in beaker 2 with agitation. An emulsion having a density of 1.80 $g/cm^3$ was obtained.

The prepared emulsion was fed to the hopper of the test apparatus, with the piston 6 positioned in the front position and with valves 3 into said pressure container due to said retrograde movement of said piston along said cylinder and 5 closed. The shear valve 7 was adjusted to give a pressure drop of 60 bars. The inlet valve 3 was opened and the piston was moved hydraulically to the rear position, whereby about 1.0 l of the emulsion was sucked into the cylinder 1. The inlet valve 3 was then closed and the outlet valve 5 opened, with the piston being simultaneously moved to the front position. This caused the emulsion to be squeezed through the shear valve 7 via the outlet valve 5 and to be collected in the receiver container 10. The emulsion sets in 2 minutes. After 24 hours the shear strength was measured to be 14,000 Pas.

We claim:

1. An apparatus for testing a shear thickening plugging fluid, characterized in that it comprises a cylinder having an inlet with an inlet valve for plugging fluid and an outlet with an outlet valve for plugging fluid, a moveable piston sealing against the cylinder wall, so that the piston by being moved rearward in the cylinder can suck plugging fluid into the cylinder through the inlet, and in a retrograde movement can press the plugging fluid out through the outlet, a shear valve connected with the outlet, which shear valve is adjustable for adjusting a desired shear stress to be subjected upon said plugging fluid, a means for measuring the pressure drop over the shear valve, a receiver means for collecting plugging fluid that has been pressed through the shear valve, and one or more means for measuring properties of the shear thickening plugging fluid.

2. The apparatus according to claim 1, characterized in that the receiver means is an open container.

3. The apparatus according to claim 1, characterized in that the receiver means is a pressure container arranged for relief of its content under a controlled pressure during the pressing in of the plugging fluid into said pressure container due to said retrograde movement of said piston along said cylinder.

4. The apparatus according to claim 1, characterized in that the receiver means contains one or more solid, permeable materials having a selected porosity and permeability.

5. The apparatus according to claim 2, characterized in that it comprises a means for measuring the shear strength of the set plugging fluid at atmospheric pressure according to standard geotechnical methods, after relief of any overpressure in the receiver means.

6. The apparatus according to claim 3, characterized in that it comprises a high pressure consistometer equipped for shear strength measuring, for measuring of the shear strength of the set plugging fluid under pressure.

7. The apparatus according to claim 4, characterized in that it comprises a means for measuring the maximum differential pressure which the content of porous material and set plugging fluid in the receiver means is capable of withstanding before the set plugging fluid collapses.

8. The apparatus according to any of claim 1, characterized in that the inlet is connected with a hopper for feeding plugging fluid from a mixing apparatus, that the shear valve is a needle valve, and that the valves and are ball valves.

9. The apparatus according to any of claim 1, characterized in that the cylinder is a double-acting hydraulic cylinder containing a drive piston which is connected with a working piston via a piston rod.

10. The apparatus according to claim 2 characterized in that the receiver means contains one or more solid, permeable materials having a selected porosity and permeability.

11. The apparatus according to claim 3 characterized in that the receiver means contains one or more solid, permeable materials having a selected porosity and permeability.

12. The apparatus according to claim 3 characterized in that it comprises a means for measuring the shear strength of the set plugging fluid at atmospheric pressure, after relief of any over pressure in the receiver means.

13. The apparatus according to claim 10 comprising a means for measuring the maximum differential pressure which the content of porous material and set plugging fluid in the receiver means is capable of withstanding before the set plugging fluid collapses.

14. The apparatus according to claim 11 comprising a means for measuring the maximum differential pressure which the content of porous material and set plugging fluid in the receiver means is capable of withstanding before the set plugging fluid collapses.

15. The apparatus according to claim 2 wherein the inlet of the cylinder is connected with a hopper for feeding plugging fluid from a mixing apparatus, that the shear valve is a needle valve, and that the inlet and outlet valves are ball valves.

16. The apparatus according to claim 7 characterized in that the inlet of the cylinder is connected with a hopper for feeding plugging fluid from a mixing apparatus that the shear valve is a needle valve and that the inlet valve and outlet valve are ball valves.

17. The apparatus according to claim 14 wherein the inlet of the cylinder is connected with a hopper for feeding plugging fluid from a mixing apparatus, that the shear valve is a needle valve, and that the inlet and outlet valves are ball valves.

18. The apparatus according to claim 8 characterized in that the cylinder is a double-acting hydraulic cylinder containing a drive piston which is connected with a working piston via a piston rod.

19. The apparatus according to claim 2 characterized in that the cylinder is a double-acting hydraulic cylinder containing a drive piston which is connected with a working piston via a piston rod.

20. The apparatus according to claim 17 characterized in that the cylinder is a double-acting hydraulic cylinder containing a drive piston which is connected with a working piston via a piston rod.

* * * * *